United States Patent [19]

Burton et al.

[11] Patent Number: 5,192,750

[45] Date of Patent: Mar. 9, 1993

[54] METHOD AND COMPOSITION FOR TREATMENT OF FOOD ALLERGY

[75] Inventors: Albert F. Burton, Comox; Stephen Gislason, Vancouver, both of Canada

[73] Assignee: The University of British Columbia, Vancouver, Canada

[21] Appl. No.: 826,763

[22] Filed: Jan. 28, 1992

[51] Int. Cl.$^5$ .............................................. A61K 31/70
[52] U.S. Cl. ...................................................... 514/62
[58] Field of Search ......................................... 514/62

[56] References Cited

U.S. PATENT DOCUMENTS 3,697,652 10/1972 Rovati et al. .
4,006,224 2/1977 Prudden .
4,590,067 5/1986 Meisner .

FOREIGN PATENT DOCUMENTS

WO87/02244 4/1987 PCT Int'l Appl. .

OTHER PUBLICATIONS

Olaison et al., "Abnormal Intestial Permeability in Crohn's Disease", Scand. J. Gastroenterol., 25:321-328, 1990.
Hollander et al., "Decreased Intestinal Permeability in Patients with Crohn's Disease and Their Relatives", Annals of Internal Medicine, 105:883-885, 1986.
Burton et al., "Decreased Incorporation of $^{14}$C-- Glucosamine Relative to $^3$H-N-Acetyl Glucosamine in the Intestinal Mucosa of Patients with Inflammatory Bowel Disease", Amer. Journal of Gastroenterology, vol. 78, No. 1, pp. 19-22, 1983.
Peters et al., "Uses and abuses of intestinal permeability measurements", Canadian Journal of Gastroenterology, 2:127-132, 1988.

Primary Examiner—Leonard Schenkman
Attorney, Agent, or Firm—Barrigar & Oyen

[57] ABSTRACT

This invention pertains to the novel use of N-acetyl glucosamine to minimize or eliminate food intolerance or food allergy symptoms in human beings afflicted with these symptoms by maintaining the integrity and normal function of the gastrointestinal tract in such human beings. A method of alleviating food sensitivity and food allergy in a human being comprising feeding the human being a therapeutic amount of N-acetyl glucosamine on a periodic basis.

7 Claims, No Drawings

METHOD AND COMPOSITION FOR TREATMENT OF FOOD ALLERGY

FIELD OF THE INVENTION

This invention pertains to the novel use of N-acetyl glucosamine to minimize or eliminate food intolerance or food allergy symptoms in human beings afflicted with these symptoms by maintaining the integrity and normal function of the gastrointestinal tract in such human beings.

BACKGROUND OF THE INVENTION

Food intolerance of some kind is very common in human beings. Food allergies are also common. The majority of human beings have an intolerance of certain constituents of foods. About 5 percent of the population have reactions to ingested substances which are sufficiently serious to require medical attention. These reactions can in some instances be life-threatening. For instance, in a widely publicized case, a bride with a chronic peanut allergy died in the United States in 1990 within minutes of consuming some wedding cake that had been baked with peanut oil as a pan grease.

In recent years evidence has mounted that the basic cause of food intolerance is the absorption of substances which are normally excluded but which in susceptible individuals are absorbed by the gastrointestinal tract because of defects in the tissue which lines the digestive tract (Peters, T. F., Bjarnason, I., Canadian Journal of Gastroenterology 1988, 2: 127–132; Olaison et al., Scandinavian Journal of Gastroenterology 1990, 25: 321–328; Hollander et al., Annals of Internal Medicine, 1986, 105: 883–885).

It is becoming increasingly clear that this basic tissue defect underlies disorders of the gastrointestinal tract which can range from mild food intolerance to, in more severe cases, erosion and ultimately ulceration of the mucosa. Persons with Inflammatory Bowel Disease, which represents the more severe situation, usually also have other symptoms which relate to food allergy.

The manifestation of food allergy can involve virtually any tissue in the body. The respiratory tract is involved in many inhaled allergies affecting the eyes, ears, mouth, upper respiratory tract and the lungs. Because of the very large absorptive area in the gastrointestinal tract, it is probably the major site of absorption of offending substances. Many of the symptoms of food allergies are manifest in the digestive tract itself, but might involve any other tissues, including the brain, and, accordingly, affect behaviour.

The most successful treatment of food allergy to date is the avoidance of offending substances once they have been identified. This requires diet revision, usually involving strict restrictive measures. Most promising is the use of Elemental diets which exclude all naturally-occurring potential allergens by providing a diet of essential nutrients in their simplest form, that is, in small molecules which are readily absorbed such as food which has been digested by the action of digestive enzymes in the gut. These diets remove the offensive substances, and have proven to be highly successful in long-term treatment of patients with severe food allergies. About 80 percent of patients respond to these diets, but there is a relapse rate of about 10 percent each year.

Several patents disclose amino sugars for treatment of disorders.

U.S. Pat. No. 4,590,067, May 20, 1986, Meisner, Peritain Ltd., discloses a composition for preventing and treating periodontal disease comprising bone meal, ascorbic acid, tyrosine and either glucosamine or cysteine. N-acetyl glucosamine is not disclosed.

French Patent No. 2,473,887, Jul. 24, 1981, discloses the use of biochemical precursors of glucosaminegly-cans for the treatment of vascular disorders of functional or organic origin in which there is insufficient blood flow to the limbs, for asphyxic hypoxydotic symptoms, and in cosmetology, for skin defects caused by insufficient circulation to the skin. The precursors, which include N-acetylglucosamine, increase the elasticity of perivascular tissue, resulting in an increase in arterio-capillary blood flow, without having a vasodilating action.

U.S. Pat. No. 4,006,224, Feb. 1, 1977, J. F. Prudden, discloses the treatment of ulcerative colitis or regional enteritis in a mammal by administering D-glucosamine, or one of its salts. Equal or superior results to the conventional treatments of the two conditions are obtained. The dose is 20–300 mg/kg of D-glucosamine, HCl daily. In a clinical trial, a patient with Crohn's Disease that was not affected by ACTH or prednisone was given D-glucosamine, HCl subcutaneously. The symptoms stopped after several weeks of treatment.

WO A 8 702 244, N. Hendry, EP A 0178602, Peritain Ltd. and French Patent A 2016 182, Rotta Research Labratorium SpA, are of interest to this subject.

Hendry discloses a preparation for tissue growth regulation comprising (a) at least one of N-acetyl-D-glucosamine or an oligomer thereof, or a deacylated derivative thereof, or a substituted product of these compounds; (b) at least one of biotin or an analog or derivative biotin, or biologically active residue thereof; and (c) a divalent metal cation together with a pharmaceutically acceptable anion.

A key difference over the prior art is the applicant's use of N-acetyl glucosamine (NAG) as a source of amino sugar for the synthesis of molecules such as glycoproteins and glycosaminoglycans, which are rich in NAG and the synthesis of which is stimulated by NAG.

NAG is formed from glucosamine and NAG is then directly converted into other amino sugars. NAG is thus a key substance, and in the applicant's work with intestinal tissue, it was found that the formation of NAG itself from glucosamine was the slow part of the process. This necessitates the use of NAG, specifically, and not a deacetylated form, or oligomer.

NAG, moreover, is more stable than glucosamine, is a neutral substance and is readily assimilated by tissues and utilized, whereas most oligomers are not.

The proposed use of NAG is unique and differs from existing art.

An article entitled "Decreased Incorporation of $^{14}$C-Glucosamine Relative to $^{3}$H-N-Acetyl Glucosamine in the Intestinal Mucosa of Patients with Inflammatory Bowel Disease", A.F. Burton and F. H. Anderson, vol. 78, No. 1, 1983, American Journal of Gastroenterology, discloses evidence that the synthesis of glycoproteins in intestinal mucosa of patients afflicted with inflammatory bowel disease is deficient in the diseased tissues of such patients. The article discusses possible reasons for the deficiency. However, no suggestions for alleviating the deficiency are made.

SUMMARY OF THE INVENTION

The invention is directed to a method of alleviating food sensitivity and food allergy in a human being suffering from food intolerance or food allergy comprising feeding the human being a therapeutically effective amount of N-acetyl glucosamine on a periodic basis.

The N-acetyl glucosamine can be fed to the human being on a daily basis. The dosage can be about 300 mg to about 10,000 mg of N-acetyl glucosamine per day, about 1,000 mg to about 6,000 mg of N-acetyl glucosamine per day, or about 500 mg of N-acetyl glucosamine per day. The N-acetyl glucosamine can be incorporated in a pharmaceutically acceptable carrier. The N-acetyl glucosamine can be fed to the human being as required to restore the integrity of mucous membrane tissues in the body of the human being.

The invention is also directed to a composition useful for alleviating food sensitivity and food allergy in a human being comprising N-acetyl glucosamine and a pharmaceutically acceptable carrier. The N-acetyl glucosamine can be present in the amount of about 300 mg to 10,000 mg, or about 1,000 mg to about 6,000 mg.

DETAILED DESCRIPTION OF THE PREFERRED EMBODIMENT

There are tissue defects in the digestive tract of human beings suffering food intolerance or food allergies. These defects can be corrected to enable the mucosa in the tract to form a necessary barrier to transmission of food allergens and to maintain normal function. The mucosa tissue structure is rich in amino sugars derived from N-acetyl glucosamine and we have discovered that the availability of N-acetyl glucosamine is critical to its synthesis.

We have also discovered that an external source of N-acetyl glucosamine is useful to ensure adequate synthesis of the mucosal barrier. Indeed, we have found that the use of N-acetyl glucosamine alone might be sufficient in itself to treat milder food allergy cases. In more severe cases, the amino sugar, N-acetyl glucosamine might be combined with elemental diets so that the removal of offending substances is accomplished, while at the same time, providing the new amino sugar material necessary ro enable the human body to generate coherent mucosa tissue and maintain its defenses.

N-acetyl glucosamine (NAG) is an amino sugar, which is formed in all animal cells and is utilized for the synthesis of many cellular components. The biochemical process by which these components are made is similar in all cells although the end products differ depending upon the type of cell involved. Most of the end products are found outside the cells where they form sheaths which bind cells together, and are major structural components, as in the walls of blood vessels, and fill the spaces between cells, i.e. the interstitium. Amino sugars are found combined with other large molecules (macromolecules) of protein, lipid (fats) or other carbohydrates to form glycoproteins (GP), glycolipids (GL) and glycosaminoglycans (GAG). Glycoproteins have many functions, some circulate in the blood, others are anchored on the surface of cells, as are glycolipids. They can confer unique properties to the cell, for example, on the surface of red blood corpuscles there is a glycolipid which determines the blood groups A, B and O. The sole difference between these groups is the presence of a single amino sugar. Such remarkable specificity indicates that there is a "language" in which amino sugars are the "letters" analogous to the genetic code, by which biological information is recorded and put into action.

Each cell makes its own amino sugars and the process, as in the case of most biochemical synthesis, is regulated by the availability of the first member of the sequence, which in this case is glucosamine. Glucosamine is formed from the pool of sugars derived from glucose, blood sugar, and is acetylated to form N-acetyl glucosamine (NAG). NAG is the immediate precursor for two other amino sugars, N-acetyl galactosamine and N-acetyl neuraminic (sialic) acid. These amino sugars constitute about half the total weight of the GAG found in human tissues (References 1-7).

In the synthesis of these molecules, the availability of the substrate, amino sugars, is critical to proper function. We have discovered that although the formation and utilization of amino sugars takes place in all human cells independently, nevertheless an external source of amino sugar is readily taken up by the cells and is utilized by them for incorporation into the macromolecules. An external source of amino sugar, we have found, can provide for an adequate amount of substrate to satisfy cell demands which otherwise might be greater than the cells can meet.

The interstitium is the space between the cells which contains the fibrous protein collagen ensheathed by glycosaminoglycan (GAG). The GAG absorbs very large quantities of water to form a gel-like material which resists compression thereby giving shape and firmness to the tissue. This material acts as a medium which regulates the passage of nutrients, etc., between the blood and the tissues, and also acts as a barrier, for example, to the spread of infection (Bert and Pearce).

Mucous membranes are covered by a microscopically thin glycoprotein rich in sialic acid called the glycocalyx. In the gastrointestinal tract (GI), this microscopically thin layer is the ultimate barrier between the underlying tissue and the corrosive digestive juices. When the layer is damaged, erosion and ulceration of the underlying tissue occurs. If the blood supply to the upper GI is arrested for about 5 minutes, for example, it has been found that all synthetic processes cease, including formation of the glycocalyx, and an ulcer can be seen forming within an hour. This illustrates the dynamic nature of the biological processes in the human body. There are several hundred grams of amino sugar in the various tissue components of the body but the average life of a given molecule is only 3 days or so. There is thus a constant turnover of all molecules in the body, even in tissues such as bone, and a constant supply of substrates for synthesis is therefore required.

An important and novel feature of the present invention is that increased demands caused by injury such as food allergen injury can be placed upon cells which might strain their resources, and in this situation, an external supply of amino sugars is beneficial. In the gastrointestinal tract (GI), the rate of synthesis of the glycocalyx had been considered to be adequate in persons afflicted with Inflammatory Bowel Disease (IBD). However, in these persons, as in many situations where there is disease or injury, the turnover of cells is increased, perhaps as much as threefold. This creates a demand that is beyond what is considered normal. We have found that the incorporation of NAG into the intestinal mucosal tissue is three times greater in persons afflicted with IBD than in those who are not afflicted.

We have also found that in human placenta near term, the formation of glycosaminoglycan (GAG) is stimulated strongly by the steroid 17 α-hydroxyprogesterone (Burton et al.) which appears to function by increasing the synthesis of amino sugars. We have discovered that the same stimulation can be achieved merely by providing the appropriate amino sugars.

Others have shown that in chondrocytes, the cells which form cartilage, the presence of corticosteroids inhibits the formation of GAG. Supplying amino sugars largely overcame this inhibition (Fassbender).

In a recent publication, the question of intestinal permeability in persons with Crohn's Disease, a form of IBD, was reviewed (Olaison et al.). It was found that these persons have greater than normal permeability of the GI tract which leads to the absorption into the bloodstream of substances normally excluded. This includes the substances which cause food sensitivities or food allergies. The condition is attributed to a defect in the mucosal barrier, the glycocalyx, and the intercellular cement composed of GG. Even unaffected relatives of these patients have been found to have increased permeability (Hollander et al.) which supports the concept that some individuals have a genetic or constitutional defect which sets the stage for a spectrum of disorders ranging from mild to serious food intolerance to severe inflammatory lesions.

Various agents inhibit the formation of the mucosal barrier including ethanol, aspirin and other antiinflammatory agents. Erosion and bleeding of the GI tract is a major side-effect of such drugs. An agent, proglumide, which protects against ulcer formation has been shown to stimulate the incorporation of NAG into mucosal glycocalyx and this is considered the reason for its effectiveness (Umetsu).

Inflammation is a common accompaniment of many forms of injury and is part of the body's defense and repair mechanism. Often, however, the inciting agent is such that the inflammation serves no protective purpose and in fact results in tissue damage causing pain and disability, as in arthritis.

There are, therefore, many situations where an external source of amino sugar can be beneficial. We have discovered that a good choice is N-acetyl glucosamine (NAG) which is a neutral compound, is stable, is very soluble, is tasteless, and is readily absorbed from the digestive tract. It circulates in the blood with a half-life about 4 hours and very little is excreted since it is a "committed metabolite" utilized exclusively for the synthesis of GP, GL, GAG in tissue components. An external supply, we have found, is readily taken up and utilized by the human body and therefore has the potential to be of benefit in many situations where the synthetic processes are less than adequate to meet demands. NAG alone is capable of efficient utilization for these processes when taken by mouth.

EXAMPLE 1

Case History—G.E.D.

G.E.D. is professor emeritus of the Faculty of Medicine, The University of British Columbia, Vancouver, B.C., Canada. For many years, G.E.D. suffered from a variety of food sensitivities. Reactions had sometimes been dramatic, and even at one instance put him in the Emergency Department at Vancouver General Hospital, Vancouver, B.C., Canada. The sensitivities started with orange juice, but subsequently expanded to include meat, milk products, corn, etc. G.E.D. had been able to control them, for the most part, by adhering closely to a rotation of dietary components every four days and refraining from eating in restaurants. Gradually, his symptoms abated but he still had episodes of pain and discomfort that he attributed to dietary causes. In November, 1990, he received a trial supply of N-acetyl glucosamine (NAG), taking it with him on a trip to California, Texas and Florida. Whereas normally he would have expected at least some dietary and food sensitivity problems on such a trip, he experienced none. Since then, he has been much less troubled by symptoms, and these have quickly abated whenever he took a dosage of NAG.

Because of the variability of his response to food, it has taken some months to evaluate the effect of NAG, but G.E.D. is positive it helps considerably. Recently, his daughter, who has similar problems, had persistent pain after drinking orange juice. This intestinal pain responded quickly to ingestion of the NAG that G.E.D. gave her.

EXAMPLE 2

Case History—TG

Male, 68, experienced chronic constipation and intolerance of some foods, which had been attributed to deficient secretion of mucous in the gastrointestinal tract. He began taking NAG, 3 g per day, in 1988 and reported normalization of bowel function without the need for oil or other laxatives. His tolerance of foods improved simultaneously and he also reported that a nasal allergy improved greatly. Symptoms recurred in one to two weeks when his supply of NAG ran out but came under control in a week or two upon resuming NAG. He claims he needs at least 3 g of NAG per day for effective control.

EXAMPLE 3

Case History—TL

T.L., male, age 23, began suffering sharp abdominal pain in 1985, and a general intolerance of foods except for rice and a few other things. He could not tolerate fibre, fried foods, etc. He was prescribed an anti-ulcer regime which caused little improvement. In 1987, he was given cimetidine and sulcrate, anti-ulcer agents. Colonoscopy and gastroduodenoscopy in 1987–1988 were negative. He was also diagnosed as asthmatic, and allergic to grass, dust, trees, hair and some foods.

T.L. began ingesting NAG at a rate of 3 g per day in Oct., 1988. His symptoms improved in three weeks. He continued NAG treatment and reported that at eight months, his symptoms had all been alleviated, including the asthma. He continues to have some sensitivity to caffeine and alcohol, which he avoids, but he can now eat a wide variety of foods including salads and high-fibre items, without difficulty. T.L. no longer suffers nausea and "heaving" each morning as he did previously and feels in good health. He has gained 5 kg and has, since 1988, successfully completed the last two years of a degree at The University of British Columbia.

EXAMPLE 4

Case History—S.C.

S.C., female, age 45, had been experiencing food intolerance, including gluten sensitivity. She tried various diets without much success. She began in 1989 to take NAG at 3 g per day. She continued for three months and noticed considerable reduction in food intolerance. Thereafter, she tried other diets without NAG for a year. At that time, she concluded that the NAG treatment was superior to the other dietary measures and resumed NAG treatment late in 1990. S.C. reported that daily NAG treatment enabled her to eat a wider variety of foods without experiencing difficulties as before, and that it has greatly improved her condition.

EXAMPLE 5

Case History—W.R.

W.R., male, age 46, has had Crohn's Disease since the age of 18. W.R. underwent surgery on three occasions with removal of considerable bowel. He suffered subsequently from near-intestinal blockage on several occasions since 1981, and pain and bloating of the intestinal tract almost continuously. He took imodium and prednisone (a corticosteroid). Physicians were reluctant to perform more surgery. W.R. began taking NAG in 1989 and felt that it began to improve his condition in a week or so. He experienced less pain and noted a great increase in his ability to tolerate a wider variety of food which previously would cause severe symptoms. W.R. underwent surgery again in 1989 for residual damage caused by earlier bouts of inflammation. He then resumed ingesting NAG at a rate of 3 to 4 g per day and reports that it is highly effective in controlling his symptoms.

EXAMPLE 6

Case History S.B.

S.B., female, 55, underwent surgery for Crohn's Disease in 1977, with removal of about 1 m of her terminal ileum. Subsequently, she experienced considerable pain, discomfort, nausea and diarrhea. Cholestyramine has helped the diarrhea by eliminating excess bile salts; she also requires injections of vitamin B12 because of the loss of terminal ileum. She began taking NAG late in 1977, initially at 1 g or so daily, ranging up to 10 g. Usually, she finds about 3 g per day is sufficient to cause marked improvement in digestion, better tolerance of foods, little diarrhea and much improvement in her discomfort level.

She has taken NAG with the approval of her physician for over eleven years and has maintained a reasonably stable condition. S.B. has had intermittent problems, including surgery for abscess, kidney stone, hysterectomy, residual effects of the Crohn's Disease, and the surgeons have reported finding no evidence for active Crohn's Disease. Numerous laboratory and organ function tests have been performed since she started taking NAG. Except for a tendency to require supplements of potassium, other tests have been normal, including blood, urine, thyroid and kidney function. S.B. has held a very responsible position for the past ten years, which she attributes largely to the benefits of NAG in her diet. She would not be able to handle the situation without daily NAG treatment.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Balazs, E. A., Jeanloz, R. W.: The Amino Sugars. Academic Press, New York, 1965, vol. IIA.
2. Heinegard, D., Paulsson, M.: Extracellular Matrix Biochemistry. Piez, K. A., Reddi, A. H. eds., Elsevier, New York, 1984.
3. Varma, R., Varma, R. S.: Mucopolysaccharides—Glycosaminoglycans—of Body Fluids in Health and Disease. W. de Gruyter, New York, 1983.
4. Schachter, H.: Biosynthetic controls that determine the branching and microheterogeneity of protein-bound oligosaccharides. Biochemistry and Cell Biology 1986, 64: 163-181.
5. Lukie, B. E., Forstner, G. G.: Synthesis of intestinal glycoprotein. Incorporation of $^{14}$C-glucosamine in vitro Biochimica et Biophysica Acta 1972, 261: 353-364.
6. Bert, J. L., Pearce, R. H.: The Interstitium and Microvascular Exchange. Handbook of Physiology—The Cardiovascular System IV, 1984, 521-547.
7. Zubay, G.: Biochemistry 2nd ed. MacMillan Publishing Co., New York, 1988, 663.
8. Burton, A. F., Anderson, F. H.: Decreased incorporation of $^{14}$C-glucosamine relative to $^{3}$H-N-acetyl glucosamine in the intestinal mucosa of patients with inflammatory bowel disease. American Journal of Gastroenterology 1983, 78: 19-22.
9. Burton, A.f., Lockhart, F., Bosnjak, S., Yong, S.: Stimulation by 17-alpha-hydroxyprogesterone of glycoprotein and glycosoaminoglycan synthesis in human placenta in vitro. Biology of the Neonate 1989, 55:151-155.
10. Fassbender, H. G.: Role of chondrocytes in the development of osteoarthritis. American Journal of Medicine 1987, 83 (supp. 5A) 17-24.
11. Olaison, G., Sjodahl, R., Tagesson, C.: Abnormal Intestinal Permeability in Crohn's Disease. Scandinavian Journal of Gatroenterology, 1990, 25: 321-328.
12. Hollander, D. et al.: Increased intestinal permeability in patients with Crohn's Disease and their relatives. Annals of Internal Medicine 1986, 105: 883-885.
13. Umetsu, T. et al.: Effect of proglumide on glycoprotein synthesis in aspirin-induced gastric erosions in rats. European Journal of Pharmacology 1980, 69: 69-77.

We claim:

1. A method of alleviating food sensitivity and food allergy in a human being suffering from food intolerance or food allergy comprising feeding said human being a therapeutically effective amount of N-acetyl-glucosamine as required to alleviate food sensitivity or food allergy in said human being.
2. A method according to claim 1 wherein the N-acetyl glucosamine is fed to the human being on a daily basis.
3. A method according to claim 1 wherein the human being is fed about 300 mg to about 10,000 mg of N-acetyl glucosamine per day.
4. A method according to claim 1 wherein the human being is fed about 1,000 mg to about 6,000 mg of N-acetyl glucosamine per day.
5. A method according to claim 1 wherein the human being is fed about 500 mg of N-acetyl glucosamine per day.
6. A method according to claim 4 wherein the N-acetyl glucosamine is incorporated in a pharmaceutically acceptable carrier.
7. A method according to claim 1 wherein the N-acetyl glucosamine is fed to the human being as required to restore the integrity of mucous membrane tissues in the body of the human being.

* * * * *